US011010591B2

(12) United States Patent
Ghafurian et al.

(10) Patent No.: US 11,010,591 B2
(45) Date of Patent: May 18, 2021

(54) AUTOMATIC PROTEIN CRYSTALLIZATION TRIAL ANALYSIS SYSTEM

(71) Applicant: Merck Sharp & Dohme Corp., Rahway, NJ (US)

(72) Inventors: Soheil Ghafurian, Brooklyn, NY (US); Ilknur Icke, Attleboro, MA (US); Charles A. Lesburg, Newton, MA (US); Belma Dogdas, Ridgewood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 137 days.

(21) Appl. No.: 16/265,730

(22) Filed: Feb. 1, 2019

(65) Prior Publication Data
US 2020/0250397 A1    Aug. 6, 2020

(51) Int. Cl.
| | | |
|---|---|---|
| *G06K 9/00* | (2006.01) | |
| *G06K 9/62* | (2006.01) | |
| *G06T 3/60* | (2006.01) | |
| *G06N 3/08* | (2006.01) | |
| *G06N 3/04* | (2006.01) | |
| *G01N 21/84* | (2006.01) | |
| *G01N 33/483* | (2006.01) | |
| *G06F 3/0484* | (2013.01) | |

(52) U.S. Cl.
CPC ......... *G06K 9/00147* (2013.01); *G01N 21/84* (2013.01); *G01N 33/483* (2013.01); *G06K 9/00134* (2013.01); *G06K 9/628* (2013.01); *G06K 9/6257* (2013.01); *G06K 9/6262* (2013.01); *G06K 9/6277* (2013.01); *G06N 3/04* (2013.01); *G06N 3/08* (2013.01); *G06T 3/60* (2013.01); *G01N 2021/8477* (2013.01); *G06F 3/04842* (2013.01)

(58) Field of Classification Search
None
See application file for complete search history.

(56) References Cited

U.S. PATENT DOCUMENTS

2004/0218804 A1* 11/2004 Affleck .............. G02B 21/0016
382/141

OTHER PUBLICATIONS

Adabi, M. et al., "Tensofflow: Large-scale Machine Learning on Heterogeneous Distributed Systems," arXiv preprint arXiv:1603.04467, Mar. 16, 2016, 19 pages.

(Continued)

*Primary Examiner* — Leon Flores
(74) *Attorney, Agent, or Firm* — Fenwick & West LLP

(57) ABSTRACT

A protein crystallization trial is automatically analyzed by capturing images of the protein drops in the trial. A machine-learned model, such as a neural network, is applied to classify the images. The model generates a predicted classification from among a set of possible classifications which includes one or more crystal type classifications and one or more non-crystal type classifications. Users may be notified automatically of newly identified crystals (e.g., drops that are classified as a crystal type). The notification may include a link to a user interface that includes results of the trial.

20 Claims, 8 Drawing Sheets

(56) References Cited

OTHER PUBLICATIONS

Bern, M. et al., "Automatic classification of protein crystallization images using a curve-tracking algorithm," Journal of Applied Crystallography, Apr. 2004, pp. 279-287, vol. 37, No. 2.
Buduma, N. et al., "Fundamentals of Deep Learning: Designing Next-generation Machine Intelligence Algorithms," O'Reilly Media, Inc., Jun. 2017, seven pages (with cover page and table of contents).
Cumbaa, C.A. et al., "Protein crystallization analysis on the World Community Grid," Journal of Structural and Functional Genomics, Mar. 2010, pp. 61-69, vol. 11, No. 1.
Damien, A. et al., "TFLearn: Deep learning library featuring a higher-level API for TensorFlow," 2016, four pages, [Online] [Retrieved on Feb. 7, 2020], Retrieved from the Internet<URL: https://github.com/tflearn/tflearn>.
Deng, J. et al., "ImageNet: A Large-Scale Hierarchical Image Database," 2009 IEEE Conference on Computer Vision and Pattern Recognition, Jun. 20, 2009, pp. 248-255.
Ghafurian, S. et al., "Automated Classification of Protein Crystallization X-Ray Images Using Deep Convolutional Neural Networks,"2018 IEEE 15th International Symposium on Biomedical Imaging (IBSI), 2018, one page.
Ghafurian, S. et al., "Classification of Protein Crystallization X-Ray Images Using Major Convolutional Neural Network Architectures," arXiv:1805.04563, May 11, 2018, 18 pages (with supplemental material).
He, K. et al., "Deep Residual Learning for Image Recognition," In Proceedings of the IEEE Conference on computer vision and pattern recognition, 2016, pp. 770-778.
Hung, J. et al., "Protein crystallization image classification with Elastic Net," In Medical Imaging: Image Processing, Mar. 2014, 14 pages, vol. 9034.
Krizhevsky, A. et al., "ImageNet Classification with Deep Convolutional Neural Networks," In Advances in neural information processing systems, 2012, pp. 1097-1105.
Lin, M. et al., "Network in Network," arXiv preprint arXiv:1312.4400, Dec. 2013, 10 pages.
Liu, R. et al., "Image-based crystal detection: a machine-learning approach," Biological Crystallography, Dec. 2008, pp. 1187-1195, vol. 64, Part 12.
Luft, J. R. et al., "Efficient optimization of crystallization conditions by manipulation of drop volume ratio and temperature," Protein Science, Apr. 2007, pp. 715-722, vol. 16, No. 4.
Luft, J.R. et al., "What's in a Drop? Correlating Observations and Outcomes to Guide Macromolecular Crystallization Experiments," Crystal Growth & Design, Mar. 2011, pp. 651-663, vol. 11, No. 3.
Rhodes, G., "Crystallography Made Crystal Clear," Academic Press, Inc., 2006, seven pages (with cover page and table of contents).
Sigdel, M. et al., "Feature analysis for classification of trace fluorescent labeled protein crystallization images," BioData Mining, Dec. 2017, 35 pages, vol. 10, No. 1.
Sigdel, M. et al., "Real-Time Protein Crystallization Image Acquisition and Classification System," Crystal Growth & Design, Jul. 3, 2013, pp. 2728-2736, vol. 13, No. 7.
Simonyan, K. et al., "Very Deep Convolutional Networks for Large-Scale Image Recognition," arXiv eprint arXiv:1409.1556, Sep. 2014, 12 pages.
Snell, E.H. et al., "Establishing a training set through the visual analysis of crystallization trials. Part I: ~150,000images," Acta Crystallographica Section D: Biological Crystallography, Nov. 2008, pp. 1123-1130, vol. 64, No. 11, , with supplemental material.
Snell, E.H. et al., "Establishing a training set through the visual analysis of crystallization trials. Part II: crystal examples," Acta Crystallographica Section D: Biological Crystallography, Nov. 2008, pp. 1131-1137, vol. 64, No. 11.
Szegedy, C. et al., "Going Deeper with Convolutions," 2015 IEEE Conference on Computer Vision and Pattern Recognition (CVPR), Jun. 7-12, 2015, nine pages, Boston, MA, USA.
Szegedy, C. et al., "Rethinking the Inception Architecture for Computer Vision," 2016 IEEE Conference on Computer Vision and Pattern Recognition (CVPR), Jun. 27-30, 2016, pp. 2818-2826, Las Vegas, NV, USA.
Yann, M. L.-J. et al., "Learning Deep Convolutional Neural Networks for X-Ray Protein Crystallization Image Analysis," AAAI '16: Proceedings of the Thirtieth AAAI Conference on Artificial Intelligence, Feb. 2016, pp. 1373-1379.
Zeiler, M. D. et al., "Visualizing and Understanding Convolutional Networks," 13th European Conference on Computer Vision (ECCV), Sep. 6-12, 2014, pp. 818-833, Zurich, Switzerland.

* cited by examiner

| Score | Barcode | Well | Drop ☑1☑2☑3 | Temp | Thumbnail | Dispute | Conditions Search | Time (days) |
|---|---|---|---|---|---|---|---|---|
| 0.83 | 93G2 | H12 | 3 | 20 | | | 0.1M BICINE pH, 2v/v Dioxane, 10w/v PEG 20K | 22 |
| 0.73 | 93G2 | G1 | 1 | 20 | | | 0.1M HEPES pH 7.5, 1.5M LiSO4 | 6 |
| 0.51 | 93G2 | D2 | 2 | 20 | | | 0.1M Na3 Cit pH 6.7, 25v/v 2-PropOH, 20w/v 2K | 138 |
| 0.35 | 93G2 | H4 | 3 | 20 | | | 0.01M CoCl2, 0.1 NES pH 7.2, 1.8M (NH4)2SO4 | 46 |

☑ Crystal  ☑ Not Sure  ☑ Non Crystal

FIG. 6

AUTOMATIC PROTEIN CRYSTALLIZATION TRIAL ANALYSIS SYSTEM

TECHNICAL FIELD

The present disclosure relates to protein crystallization trials, and in particular to automatic computer-based identification of trials in which protein crystals have formed.

BACKGROUND

The molecular structure of proteins is studied using x-ray crystallography. As the name implies, this technique requires the protein of interest to be in a crystallized form. However, the conditions under which a given protein will crystallize are often highly specific and difficult to predict. For example, achieving protein crystallization may involve fine tuning the concentration, temperature, precipitant type, and pH value. Furthermore, the time it takes for crystals to form and the nature of those crystals may also be highly dependent on the specific protein being studied.

Existing robotic systems for identifying crystallization conditions of a protein perform large numbers trials under a wide range of conditions. However, each trial must be manually inspected periodically (e.g., daily) to determine whether crystallization has occurred. In a majority of the trials, no crystallization will ever occur as the conditions are not conducive to crystallization of the particular protein being tested. As a result, protein x-ray crystallographers spend a significant proportion of their working day inspecting trials to identify crystals rather than analyzing the molecular structure of proteins of interest.

SUMMARY

Embodiments relate to automatic analysis of protein crystallization trials. A camera captures images of the protein drops in the trial and a machine-learned model, such as a neural network, classifies the images. The potential classifications for images include one or more crystal type classifications and one or more non-crystal type classifications. Users may be notified automatically of newly identified crystals (e.g., drops that are classified as a crystal type). The notification may include a link to a user interface that includes results of the trial.

In various embodiments, a method of automatically analyzing protein crystallization trials includes retrieving an image depicting a drop including a protein in solution from a datastore. The method also includes applying a neural network to predict a classification for the image and determining whether the protein has crystallized in the drop based on the predicted classification. The neural network includes a plurality of dimensionality reduction layer pairs and a plurality of fully connected layers. The method further includes providing a user interface for display at a client device in response to detecting the protein has crystallized. The user interface includes information about the drop.

The dimensionality reduction layer pairs may include a convolution layer followed by a max-pooling layer. In one example, the neural network includes five dimensionality reduction layer pairs and/or four fully connected layers. The output from the neural network may include the predicted classification and a score indicating a likelihood that the predicted classification is correct. Alternatively, the output from the neural network may include a set of scores, each score indicating a likelihood that a corresponding one of a plurality of possible classifications is correct. The plurality of possible classifications may include a plurality of crystal type classifications and a plurality of non-crystal type classifications. As another example, a ResNet-56 model may be used.

The neural network may be trained by a process that includes labelling a training set of images in which each image is labelled with one of a plurality of classifications. The classifications may include one or more crystal type classifications and one or more non-crystal type classifications. The process also includes augmenting the training set by generating synthetic images for the one or more crystal type classifications and applying the neural network to the augmented training set to generate predicted classifications for the images from among the plurality of classifications. The process further includes updating the model based on differences between the labels and the predicted classifications for the images in the training set.

In one embodiment, generating a synthetic image for a given classification includes identifying an image labelled with the given classification, rotating the identified image through a random angle, flipping the identified image horizontally with a probability of 50%, and flipping the identified image vertically with a probability of 50%.

In one embodiment, if protein crystallization is determined to have occurred in the drop, the method also includes identifying a user subscribed to receive updates for a trial with which the image is associated, looking up contact information for the user, and sending a notification that the protein has crystallized in the drop to the user using the contact information. The user interface may be provided at a client device in response to user selection of the link included in the notification.

In other embodiments, an automatic protein crystallization trial analysis system is stored on a machine-readable storage medium. The automatic protein crystallization trial analysis system is manufactured by a process including retrieving a training set of images depicting drops including a protein in solution from a datastore. The process further includes labelling the images in the training set with one of a set of classifications including one or more crystal type classifications and one or more non-crystal type classifications. The training set is augmented by generating synthetic images for the one or more crystal type classifications and a model is trained to classify images according to the plurality of classifications using the augmented training set.

In further embodiments, a protein trial system includes a camera, a datastore, an image analysis system, and a client device. The camera periodically captures images of protein drops in a protein trial and the datastore stores the captured images. The image analysis system applies a neural network to the captured images to generate predicted classifications for the captured images. The neural network includes a plurality of dimensionality reduction layer pairs and a plurality of fully connected layers. The client device displays a user interface including the predicted classification of at least some of the captured images.

BRIEF DESCRIPTION OF DRAWINGS

The disclosed embodiments have advantages and features which will be more readily apparent from the detailed description, the appended claims, and the accompanying figures (or drawings). A brief introduction of the figures is below.

Figure (FIG. 1 is a block diagram illustrating a networked computing environment suitable for conducting protein crystallization trials, according to one embodiment.

FIG. 6 illustrates a user interface generated by the image analysis system of FIG. 4, according to one embodiment.

DETAILED DESCRIPTION

The Figures (FIGS.) and the following description relate to preferred embodiments by way of illustration only. Wherever practicable, similar or like reference numbers may be used in the figures to indicate similar or like functionality. The figures depict embodiments of the disclosed systems and methods for purposes of illustration only. One skilled in the art will readily recognize from the following description that alternative embodiments of the structures and methods illustrated herein may be employed without departing from the principles described herein.

Example Protein Crystallization Trial System

Figure 1:
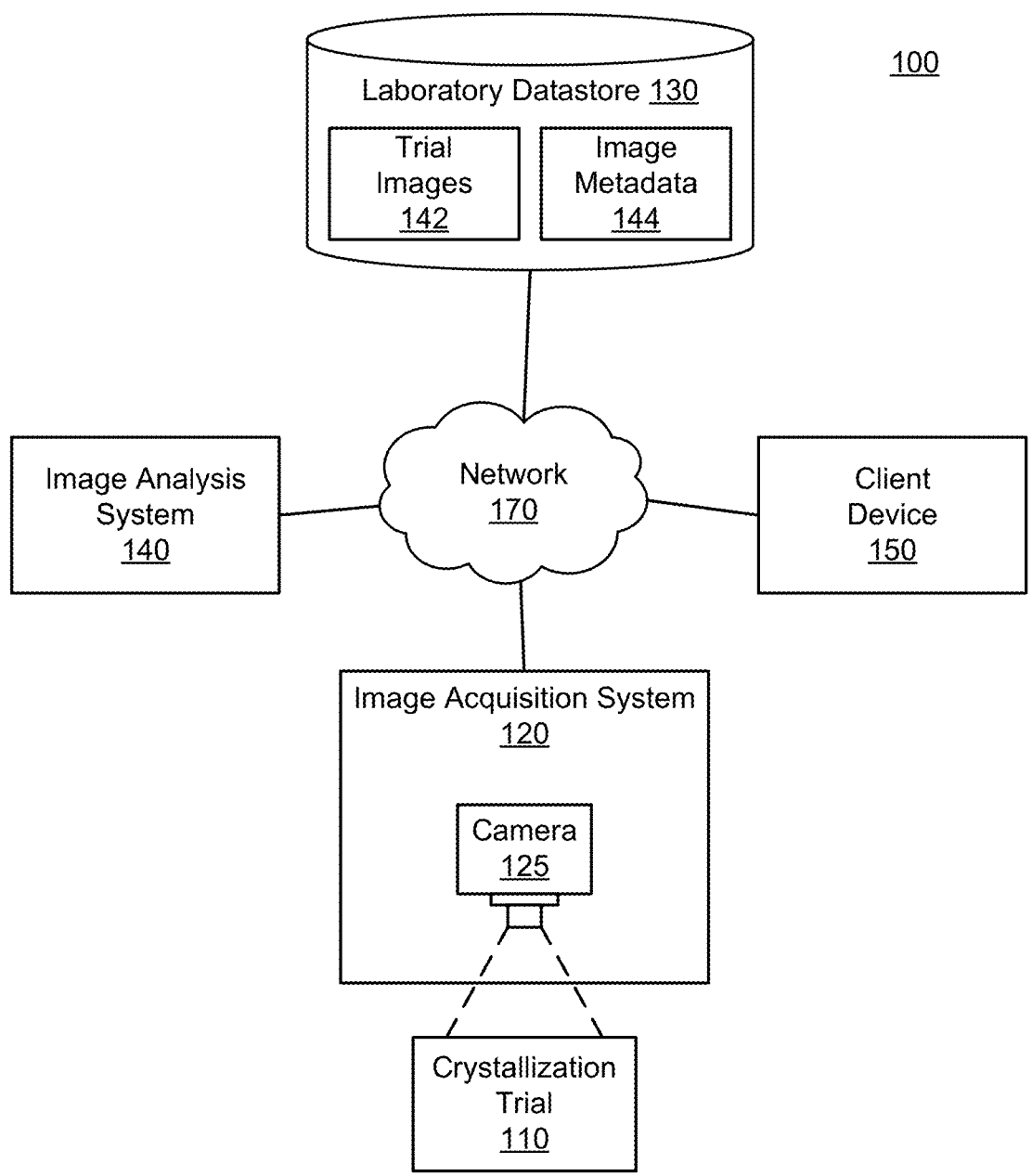

FIG. 1 shows an embodiment of a networked computing environment 100 suitable for conducting protein crystallization trials (e.g., crystallization trial 110). In the embodiment shown, the networked computing environment 100 includes an image acquisition system 120, a laboratory datastore 130, an image analysis system 140, and a client device 150, all connected via a network 170. In other embodiments, the networked computing environment 100 may include different and/or additional elements. In addition, the functions may be distributed among the elements in a different manner than described. For example, although the laboratory datastore 130 is depicted as a separate component, in some embodiments, the datastore may be part of the image acquisition system 120 and/or the image analysis system 140.

A crystallization trial 110 includes a set of drops of a protein in solution. The drops may be stored in any appropriate vessel, such as one or more 96-well plates. Each drop in the set has different conditions. For example, a trial 110 may include drops for a range of concentrations, temperatures, precipitant types, and pH values.

The image acquisition system 120 is a computer system that controls a camera 125 to capture images of drops from protein crystallization trails 110. In one embodiment, the image acquisition system 120 controls one or more robots to place a plate containing drops in the field of view of the camera. The image acquisition system 120 may then scan the camera 125 over the plate to capture individual images of each drop. In other embodiments, other methods may be used to capture images of the drops.

Figure 2:
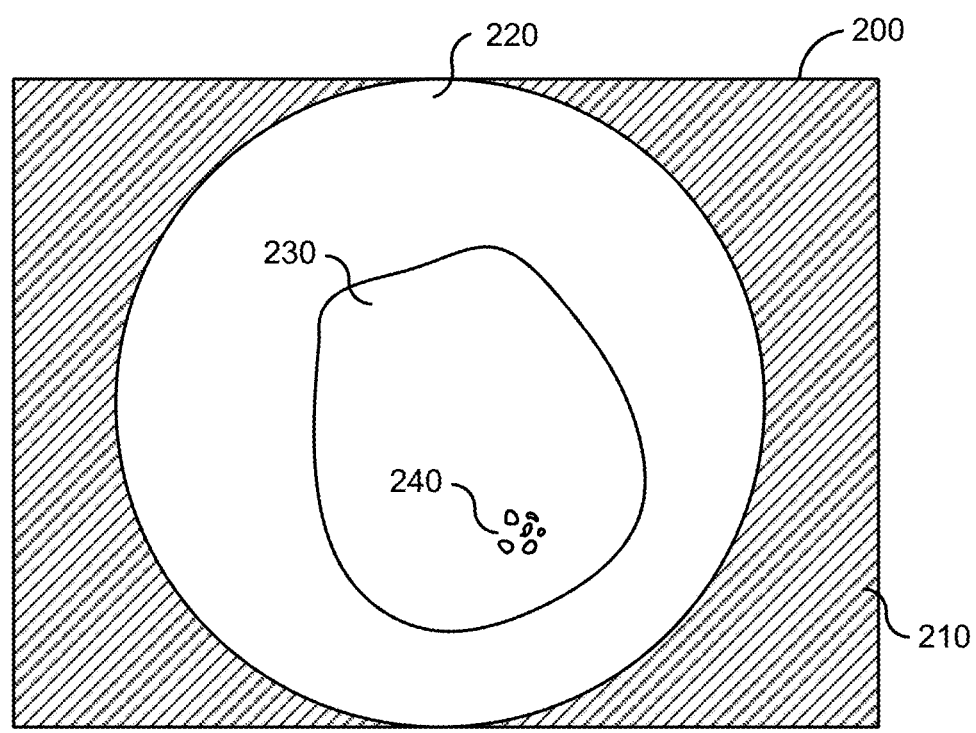
FIG. 2 illustrates an example image of a drop in a protein crystallization trial, according to one embodiment.

FIG. 2 illustrates an example image 200 captured by the camera 125. The image 200 includes a drop 230 within a well 220. In the example shown, the drop 230 includes a cluster of small features 240 that may be protein crystals or non-crystal features such as protein grains, bubbles, or precipitate. In one embodiment, the camera 125 is configured such that the well 220 fills a substantial portion of the image 200. Thus, only a relatively small amount of the plate 210 of which the well 220 is a part is included in the image 200. In other embodiments, more or less of the plate 210 (or other background features) may be included in the image 200.

Referring again to FIG. 1, the laboratory database 130 includes one or more machine-readable media configured to store sets of trial images 142 and associated image metadata 144. The trial images 142 and associated metadata 144 may be stored in a distributed database or locally by the image acquisition system 120 and/or the image analysis system 140. In one embodiment, a set of trial images 142 includes images of drops of a target protein in solution under different conditions. The set of trial images 142 may also include multiple images of each drop captured at different times. For example, the image acquisition system 120 might capture an image of each drop in a trial 110 daily (e.g., as part of a nightly update) for the duration of the trial (e.g., 60 days). A set of trial images 142 may also include multiple (e.g., three) images for each drop in each time period captured in quick succession to reduce the likelihood that all of the images for that drop in that time period are unusable.

The image metadata 144 is information about a trial images 142 stored in association with the corresponding image. The image metadata 144 may include information about the creation of the image, such as the model of the camera 125, the camera settings used, the date and time of capture, the identity of the image acquisition system 120 (e.g., a system ID), the identity of a person responsible for the trial (e.g., an employee name and/or ID), and the like. The image metadata 144 may also include information about the drop depicted in the image, such as the specific protein and conditions as well as identifiers of the plate and well the drop is in (e.g., a plate barcode and well position within the plate).

The image analysis system 140 analyzes the trial images 142 to identify drops for which crystallization has occurred. The image analysis system 140 applies a machine-learned model to classify trial images 142 as either crystal images (depicting a detectable amount of protein crystallization) or non-crystal images (not depicting a detectable amount of protein crystallization). In various embodiments, the machine-learned model does not directly classify images as either crystal or non-crystal images. Rather, the model classifies the drop in an image as having a type selected from a drop-type taxonomy that includes multiple types of both crystal and non-crystal drops.

Figure 3:
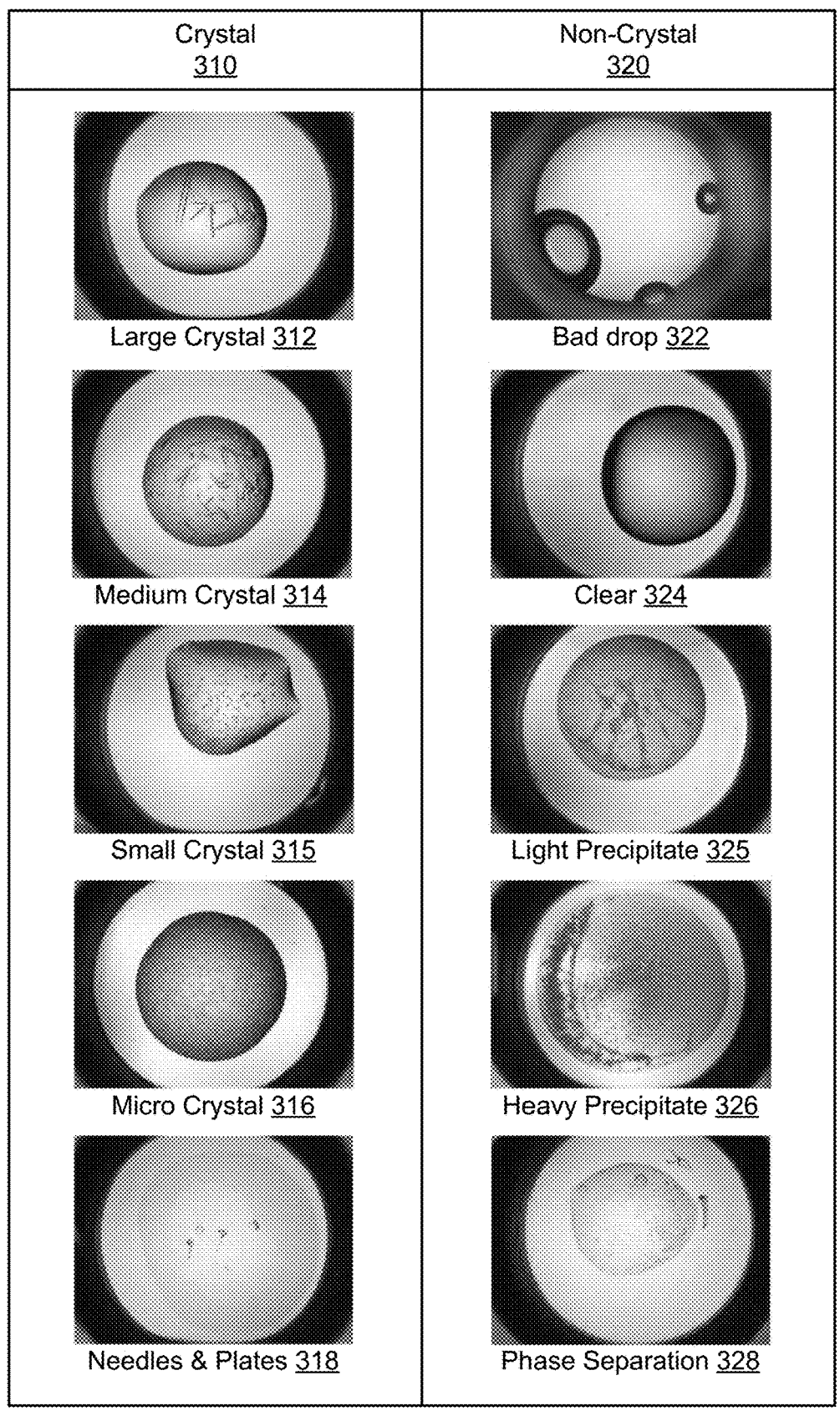
FIG. 3 is a table illustrating a taxonomy of drop types, according to one embodiment.

FIG. 3 illustrates such a taxonomy according to one embodiment in which the image analysis system 140 classifies images into one of ten types. Five of the types correspond to the presence of protein crystals 310 and five are non-crystal types 320. The five crystal types 310 include: large crystal 312, medium crystal 314, small crystal 315, micro crystal 316, and needles & plates 318. The five non-crystal types 320 include bad drop 322, clear 324, light precipitate 325, heavy precipitate 326, and phase separation 328. In other embodiments, other drop-type taxonomies may be used.

Using a taxonomy with different types of crystal 310 and non-crystal 320 may provide improved accuracy over a binary classifier (i.e., one that directly classifies images as either crystal or non-crystal) because the features indicative of one type of crystal (or non-crystal) may be significantly different from the features indicative of another type of crystal (or non-crystal). For example, in the examples shown in FIG. 3, large crystal 312 and light precipitate 325 both include elongated features whereas microcrystal 316 and clear 324 do not. Thus, the features that enable accurate distinction between these crystal 310 and non-crystal 320 types may be significantly differently.

Referring again to FIG. 1, the machine-learned model may be applied periodically over the life-cycle of a trial (e.g., hourly, daily, etc.). The image analysis system 140 may automatically notify a user or users associated with the trial if new crystal images are identified. For example, on detecting crystallization in an image of a droplet that previously had not included crystals, the image analysis system might access the metadata 144 associated with the image to identify a crystallographer responsible for the trial and send them an email, text message, instant message, or other appropriate message notifying the crystallographer of the newly detected crystals (e.g., by providing a plate bar code and well number for the drop or drops in which crystallization was detected). Embodiments of the image analysis system 140 are described in greater detail below, with reference to FIG. 4.

The client device 150 is a computing device capable of receiving user input as well as transmitting and/or receiving data via the network 170. Although only one client device 150 is shown in FIG. 1, the networked computing environment 100 may include any number of client devices. A client device 150 may be a computer system, such as a desktop or laptop computer. Alternatively, a client device 150 may be a device having computer functionality, such as a personal digital assistant (PDA), a mobile telephone, a smartphone, a tablet, or another suitable device. Note that, in some embodiments, users may view results using the same computer system that performs the analysis. In other words, the image analysis system 140 and the client device 150 may be a single computer system (which may or may not also include the laboratory datastore 130).

In one embodiment, a client device 150 executes an application enabling a user of the client device to view results generated by the image analysis system 140. For example, the client device 150 may execute a browser application to access a web-based interface provided by the image analysis system 140. In another embodiment, the client device 150 retrieves results from the image analysis system 140 and/or laboratory datastore 130 via an application programming interface (API) running on a native operating system of the client device 150, such as IOS® or ANDROID™. Embodiments of a user interface for viewing results are described in greater detail below, with reference to FIG. 6.

The network 170 provides the communication channels via which the other elements of the networked computing environment 100 communicate. The network 170 can include any combination of local area and/or wide area networks, using both wired and/or wireless communication systems. In one embodiment, the network 170 uses standard communications technologies and/or protocols. For example, the network 170 can include communication links using technologies such as Ethernet, 802.11, worldwide interoperability for microwave access (WiMAX), 3G, 4G, 5G, code division multiple access (CDMA), digital subscriber line (DSL), etc. Examples of networking protocols used for communicating via the network 170 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 170 may be represented using any suitable format, such as hypertext markup language (HTML) or extensible markup language (XML). In some embodiments, all or some of the communication links of the network 170 may be encrypted using any suitable technique or techniques.

Example Image Analysis System

Figure 4:
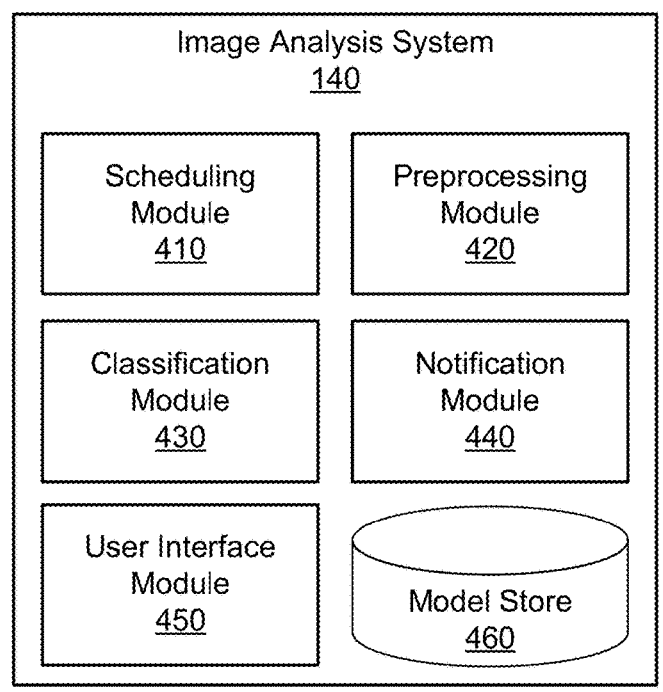
FIG. 4 is a block diagram illustrating the image analysis system 150 of FIG. 1, according to one embodiment.

FIG. 4 illustrates one embodiment of the image analysis system 140. In the embodiment shown, the image analysis system 140 includes a scheduling module 410, a preprocessing module 420, a classification module 430, a notification module 440, a user interface module 450, and a model store 460. In other embodiments, the image analysis system 140 may include different and/or additional elements. In addition, the functions may be distributed among the elements in a different manner than described. For example, in one embodiment, the scheduling module 410 is omitted and the corresponding functionality is provided by the image acquisition system 120.

The scheduling module 410 determines when the image acquisition system 120 captures images 142 for a protein crystallization trial 110. In one embodiment, images 142 of the protein drops in the trial 110 are automatically captured on a predetermined schedule (e.g., daily as part of a nightly update). In another embodiment, the scheduling module provides a user interface (e.g., accessed via a client device 150 over the network 170) with which a user may schedule when images 142 are captured for the trial 110. For example, the user may be given a choice between various image capture cycle times (e.g., hourly, twice-daily, daily, weekly, etc.) and/or be able to select specific times for an image capture cycle to begin. Each cycle, the image acquisition system 120 may capture one or more images 142 of each drop in the trial 110. Additionally or alternatively, the user may be able to manually trigger an imaging cycle (e.g., by selecting a "acquire images" button that causes an instruction to be sent to the image acquisition system 120 to begin an image capture cycle.

The preprocessing module 420 receives trial images of drops 142 (e.g., from the image acquisition system 120 or by retrieving them from the laboratory datastore 130) and preprocesses the images to prepare them for classification. In various embodiments, the preprocessing includes cropping the image 142 to make it square and/or remove background portions with little or no useful information for classification, down-sampling the image to predetermined pixel dimensions, and/or transforming the image into grayscale. Each of these transformations may enable a less complex machine-learned model used, reducing training time and computational requirements. In one embodiment, the original images 142 captured by the image acquisition system 120 are RGB images with a size of 1280×960 pixels and the preprocessing module 420 crops the edges of the image to get a 960×960 pixel portion, down-samples the cropped portion to 128×128 pixels, and transforms the down-sampled portion into grayscale. In other embodiments, different image sizes 142 and preprocessing operations may be used.

The classification module 430 classifies trial images 142 by applying a machine-learned model (e.g., retrieved from the model store 460). As described previously, the classification module 430 ultimately classifies an image 142 as either crystal 310 or non-crystal 320, which may involve classifying the image as one of a set of subtypes according to a taxonomy. In various embodiments, the machine-learned model is an artificial neural network. The neural network takes a preprocessed trial image 142 as input and outputs a predicted classification for the image. The predicted classification may be a type (e.g., this image is a small crystal type 315) or the likelihood that the image is of one or more types (e.g., there is a 70% chance that the type of the input image is micro crystal 316 and a 30% chance it is phase separation 328). Specific approaches for training the machine-learned model are described in greater detail below, with reference to FIG. 7.

Figure 5:
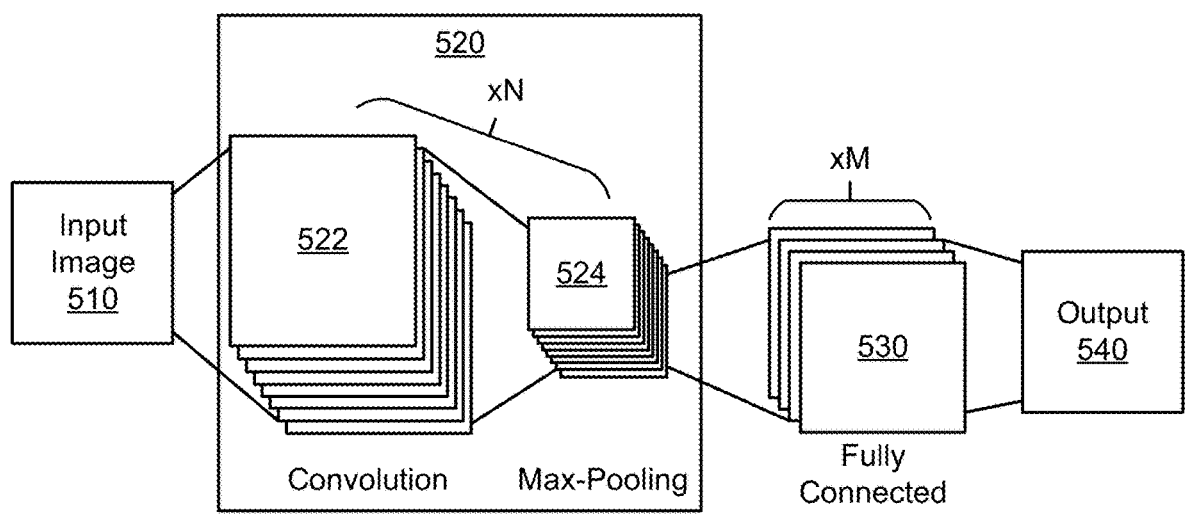
FIG. 5 is a block diagram illustrating a neural network suitable for use by the image analysis system of FIG. 4, according to one embodiment.

FIG. 5 illustrates the structure of the neural network, according to one embodiment. In the embodiment shown, an input image 510 is provided to a set 520 of one or more ("N") dimensionality reduction layer pairs. Each dimensionality reduction layer pair includes a convolution layer 522 and a max-pooling layer 524. This combination of layers reduces dimensionality by reducing the size of the feature vector that represents the input image 510. In a specific example, N is five, meaning the set 520 includes five convolution layers 522, each followed by a corresponding max-pooling layer 524. Thus, the set 520 includes a total of ten layers, alternating between a convolution layer 522 and a max-pooling layer 524.

Regardless of the number of layers in the set 520, it is followed by a set of one or more ("M") fully connected layers 530. In the embodiment shown, the output from the last max-pooling layer 524 is provided to the first fully connected layer 530. In other embodiments, additional layers may be included between the dimensionality reduction layer pairs and the fully connected layers 530. In a specific example, M is four, meaning there are four fully connected layers 530 in the neural network.

In the embodiment shown, the output 540 from the last fully connected layer 530 provides a classification for the input image 510. For example, the neural network may have an output neuron for each possible class of input image 510 that provides a score indicating the likelihood that the current input image is an example of the corresponding class. Thus, the classification module 430 may output the class with the highest score. Alternatively, the scores may be normalized to determine a probability for each possible class that the input image 510 is, in fact, an example of that class.

In another embodiment, the machine-learned model is a ResNet-56 neural network. ResNet neural networks are designed to account for the degradation that occurs as more layers are added, enabling deeper networks to be used. In particular, at the end of each convolutional layer, the input is added to the output to prevent information loss and improve network optimization. In further embodiments, other types of neural network may be used, such as CrystalNet, a Visual Geometry Group (VGG) neural network, inception-v3, or the like.

Regardless of the specific machine-learned model used, the result is an output 540 indicating the class for the input image 510 selected from a drop-type taxonomy. The class indicates whether the drop includes (or does not include) protein crystals.

Referring again to FIG. 4, regardless of the specific model used, the classification module 430 stores the results of applying the model in a data store. In one embodiment, the classification module 430 associates metadata with the trial images 142 (e.g., by adding it to the image metadata 144) indicating the classifications and corresponding scores. Alternatively, the classification module 430 may store the results separately (e.g., as a file in the model store 460).

The notification module 440 notifies users when the classification module 430 identifies drops including protein crystals. In one embodiment, the notification module 440 waits until the classification module 430 has completed classifying images 142 for a trial. If any new instances of crystallization are identified, the notification module 440 looks up contact details for any subscribed users (e.g., in the image metadata 144) and sends subscribed users notifications. For example, when setting up a new trial, a crystallographer might subscribe to receive notifications by registering an email address and the notification module 440 might send a notification to the registered email address when the classification module 430 identifies newly formed protein crystals. The notification may include a summary of the results (e.g., a number of new instances of protein crystals identified) and/or a link to view the results. Other users may be able to subscribe to receive notifications for a trial (e.g., by providing a trial ID name or number and an email address for the notifications), subject to any applicable access permissions (e.g., the user must have an email address associated with the entity running the trial).

The user interface module 450 provides a user interface for display (e.g., at a client device 150) that enables a user to view the results of a trial. In one embodiment, the user interface is a webpage accessed via the user (e.g., by clicking on a link provided in a notification generated by the notification module 440) using a browser executing on a client device 150. The user interface may present identifying information (e.g., a plate barcode and well number) for drops that the classification module 430 identified as likely to include protein crystals. The user interface may also include additional information about the drops, such as a particular crystal type, a confidence score (e.g., a percentage likelihood that the classification is correct), the conditions associated with the drop, an amount of time it took the crystals to form, and the like.

FIG. 6 illustrates one embodiment of a user interface for viewing results generated by the classification module 430. In the embodiment shown, the user interface presents results in a tabular format. Each row includes the results generated by the classification module 430 for a drop and each column includes a type of information associated with the results. A scroll bar 602 is provided (in this case, on the right-hand side) to enable the user to scroll vertically and view additional results. In some embodiments, the user interface also includes a horizontal scroll bar that enables the user to scroll horizontally and view additional columns. Zoom controls may also be provided to enable the user to zoom in and out.

In the embodiment shown, the first column 610 includes scores for the results. The score indicates the likelihood that the classification is correct. The likelihood may be that the ultimate classification of crystal or non-crystal is correct or the likelihood that the specific classification (e.g., small crystal 315, light precipitate 325 etc.) is correct. In the example results shown in FIG. 6, the results have been ranked by score, with the highest scoring result first. This may assist crystallographers in quickly identifying drops in which crystallization has occurred.

In some embodiments, the results may be divided into visually distinguishable groups based on the scores. For example, in FIG. 6, the results have been divided into three groups: likely crystallization, not sure, and likely no crystallization. Any visual distinguisher may be used to identify the groups, such as color coding (e.g., green, yellow, red), shading (e.g., light, intermediate, dark), background pattern (e.g., plain, diagonal lines, cross-hatching), etc. The groups may also be identified by physically separating them in the user interface and including them under different headings.

The user interface may also contain controls to enable the user to filter by group (e.g., checkboxes 604) and/or define the ranges of scores corresponding to each group (e.g., grouping bar 606 and sliders 607, 608). In the embodiment shown in FIG. 6, the grouping bar 606 includes a pair of sliders 607, 608. The first slider 607 sets the score value that is the boundary between the "likely crystal" group and the "not sure" group. Similarly, the second slider 608 sets the score value that is the boundary between the "not sure" group and the "likely no crystallization" group. The segments of the grouping bar 606 corresponding to each group may be visually distinguished in the same manner as results in that group to provide a more intuitive user experience.

The second column 620, third column 630, and fourth column 640 collectively identify the specific drop corresponding to the result. In the example results shown in FIG. 6, the second column 620 includes a barcode of a plate, the third column 630 identifies the well in the plate that contains the droplet, and the fourth column 640 identifies the number of the drop within the well. The fourth column 640 may also contain checkboxes 645 to enable a user to filter the results by drop number. For some experiments, success or failure of an experiment may be determined by a subset of the drops, so such checkboxes may enable more efficient review of experimental results.

The fifth column 650 includes the storage temperature for the droplet, the sixth column 660 includes a thumbnail of an image of the drop, and the seventh column 670 includes a button for the user to dispute the result generated by the classification module 430. In one embodiment, if a user selects the dispute button, a pop up opens in which the user may provide an alternate classification and/or a reason for the dispute, which the user interface module 450 sends to a laboratory manager, designated expert, or other adjudicator for resolution. Disputed classifications may also be used as feedback to update the machine-learned model.

The eighth column 680 includes the conditions associated with the drop. The conditions can include one or more parameters, such as concentration, precipitant type, pH value, etc. In the embodiment shown in FIG. 6, the eighth column 680 also includes a search box 685 that enables the user to search for results having a particular condition. For example, if the user wants to find results for a specific pH value, the user might enter that value in the search box 685 and the user interface module 450 filters the results displayed to include only those with the specified pH value listed in the corresponding conditions.

The ninth column 690 includes the number of days that have passed since the drop was created. This may help the user evaluate whether significant new crystallization or further crystallization is likely to occur in future. It may also help the user evaluate the relative value for further experimentation of different drops that include crystals. For example, all other things being equal, the user may select a set of conditions that leads to more rapid crystallization.

Referring once again to FIG. 4, the model store 460 is one or more machine-readable media configured to store the machine-learned model or models used by the classification module 430. In some embodiments, the model store 460 may also store copies of the trial images 142, image metadata 144, results, and/or any other data used by the image analysis system 140.

Example Training Method

Figure 7:
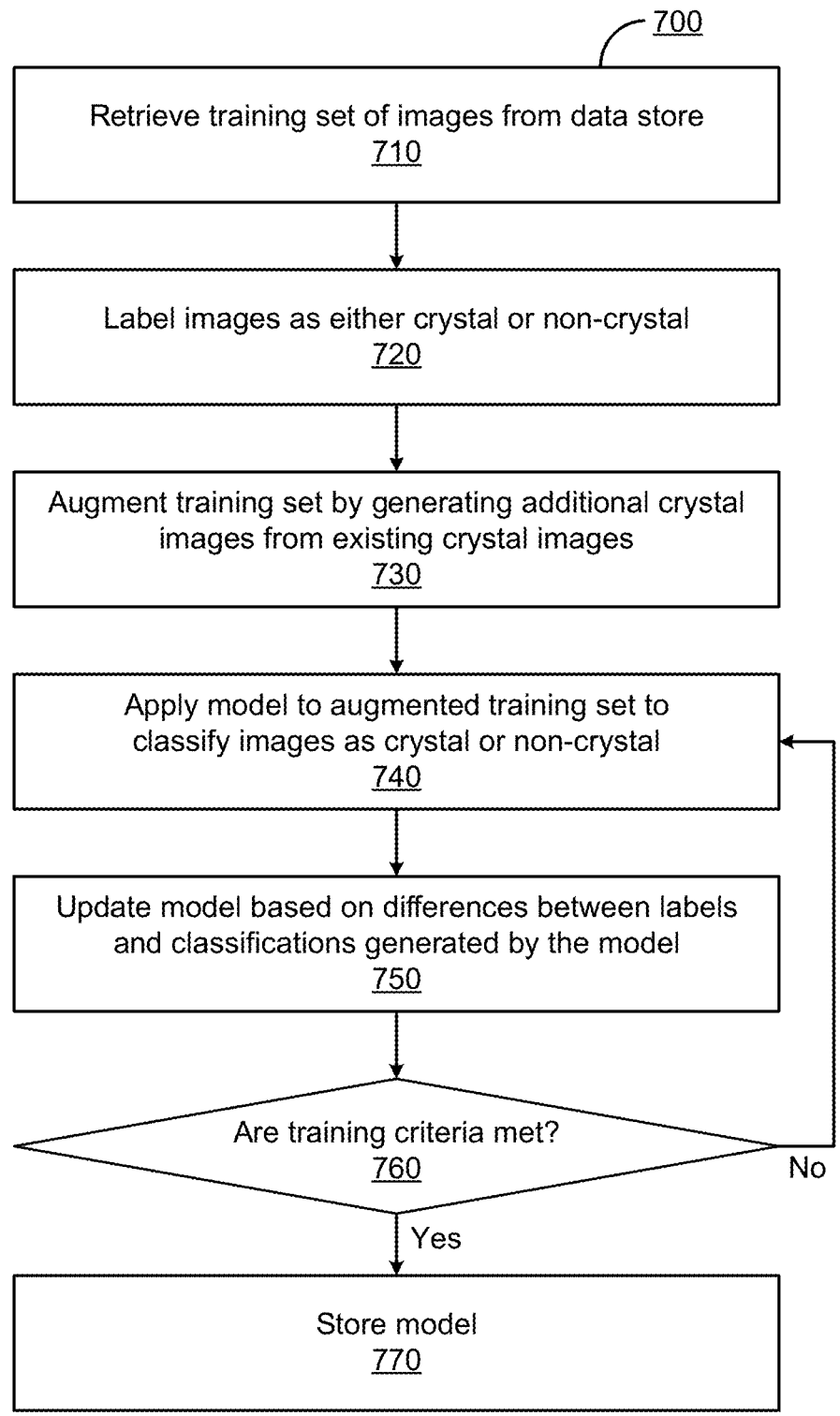
FIG. 7 is a flowchart illustrating an example method for training a model to classify images of protein crystallization trials, according to one embodiment.

FIG. 7 illustrates a method 700 for training a model for use by the classification module 430, according to one embodiment. For convenience, the method 700 is described below as being performed by a training system. The training system may be the image analysis system 140. Alternatively, the training system may be another computing system with the trained model then being installed on the image analysis system 140. For example, the trained model might be provided as part of a software package that configures the image analysis system 140 to provide some or all of the functionality described above. Some or all of the steps may be performed by other entities and/or components. Furthermore, some embodiments may perform the steps in parallel, perform the steps in different orders, or perform different steps.

In the embodiment shown in FIG. 7, the method 700 begins with the training system retrieving 710 a training set of images from a data store. Each image in the training set depicts a drop of protein in solution. Some of the images are positive examples, meaning they depict a drop in which protein crystallization has occurred, and some are negative examples, meaning no detectable crystallization has occurred in the depicted drop.

The images in the training set are labelled 720 as either a crystal type 310 or a non-crystal type 320. In one embodiment, each image is labelled as one of the ten sub-types previously described with reference to FIG. 3. The labelling may be done by human operators (e.g., crystallographers). Various techniques may be used to increase the accuracy of labelling, such as having an expert review each label, having multiple operators label each image and flagging any that different operators label differently for the review, and the like. As such, these labels may be considered as ground truth for the purposes of training.

As noted previously, because the conditions under which proteins crystallize are generally limited, there are typically many more non-crystal type 320 (negative) examples than crystal type 310 (positive) examples. This imbalance in the training set can negatively impact the training of the model. Therefore, in various embodiments, the training system augments 730 the training set (also referred to as "rebalancing") by generating additional images including crystals from those already labelled as crystal type 310.

In one embodiment, the training system creates a synthetic example of a given type of image by selecting a labelled image of that type and rotating it through a random angle. The labelled image may also be flipped horizontally and/or vertically, each with a probability of 50%. For example, the training system might generate three random numbers between zero and one, $X_1$, $X_2$, and $X_3$. The labelled image is then rotate by an angle of $360 \times X_1$ degrees, flipped horizontally if $X_2$ is less than 0.5, and flipped vertically if $X_3$ is less than 0.5.

The training system may repeat this process for generating synthetic examples until a desired number of each type have been created. The labelled image used in each iteration may be selected randomly from the available labelled images of the desired type or the training system may step through the available labelled images (e.g., generating a synthetic example from a first labelled image, then a second labelled image, then a third labelled image, etc., and returning to the first labelled image once a synthetic example has been generated from each available labelled image of the desired type). The training system may repeat the process until the total number of examples (original plus synthetic) for each crystal type is equal to the average number of examples of non-crystal types. The number of synthetic examples generated for a given type may be inversely proportional to the number of original images of that type. In one embodiment, the training system creates synthetic examples until the number of images in each category is equal to the number of images in the category with the largest number of non-synthetic examples (typically the "clear" category).

The training system applies 740 a model to the augmented training set to generate predicted classifications. In one embodiment, the model is a neural network (e.g., the neural network illustrated in FIG. 5) that outputs a score indicating the likelihood of the image being an example of each of the possible classes (e.g., the ten classes shown in FIG. 3).

The training system updates 750 the model based on differences between the predicted classifications generated by the model and the ground truth labels applied to the images. In various embodiments, the training system calculates the value of a cost function and attempts to minimize the value of the cost function (e.g., using backpropagation). In one embodiment, the training system uses the cross entropy between the predicted classifications and the ground truth labels as the cost function. In other embodiments, the cost function may be a count of the number of images incorrectly classified, a sum of error values calculated for each image (e.g., by subtracting the score the model generated for the classification matching the label from one), or any other appropriate function quantizing the difference between the ground truth labels and the predicted classifications generated by the model.

The training system determines 760 whether one or more training criteria have been met. The training criteria may include a predetermined number of training cycles (e.g., seventy), a predetermined threshold value of the cost function, a predetermined error rate, or the like. If the criteria is not met, the method 700 applies 740 the updated model to the training set again and further updates 750 the model based on the results (as described previously). If/when the training criteria are met, the training system 770 stores the model (e.g., in the model store 460).

In some embodiments, the model is validated after training. During validation, the training system applies the trained model to a set of labelled images that is distinct from the training set to determine an accuracy (e.g., a percentage of images correctly classified). This process may help determine whether the model has truly been trained to classify images of each class or whether the model is overfitted to specifically classify the training set but is inaccurate with regard to previously unseen images. Assuming the model is successfully validated (e.g., its accuracy exceeds a required accuracy threshold), the model is ready for use in classifying unlabeled images.

Example Image Classification Method

Figure 8:
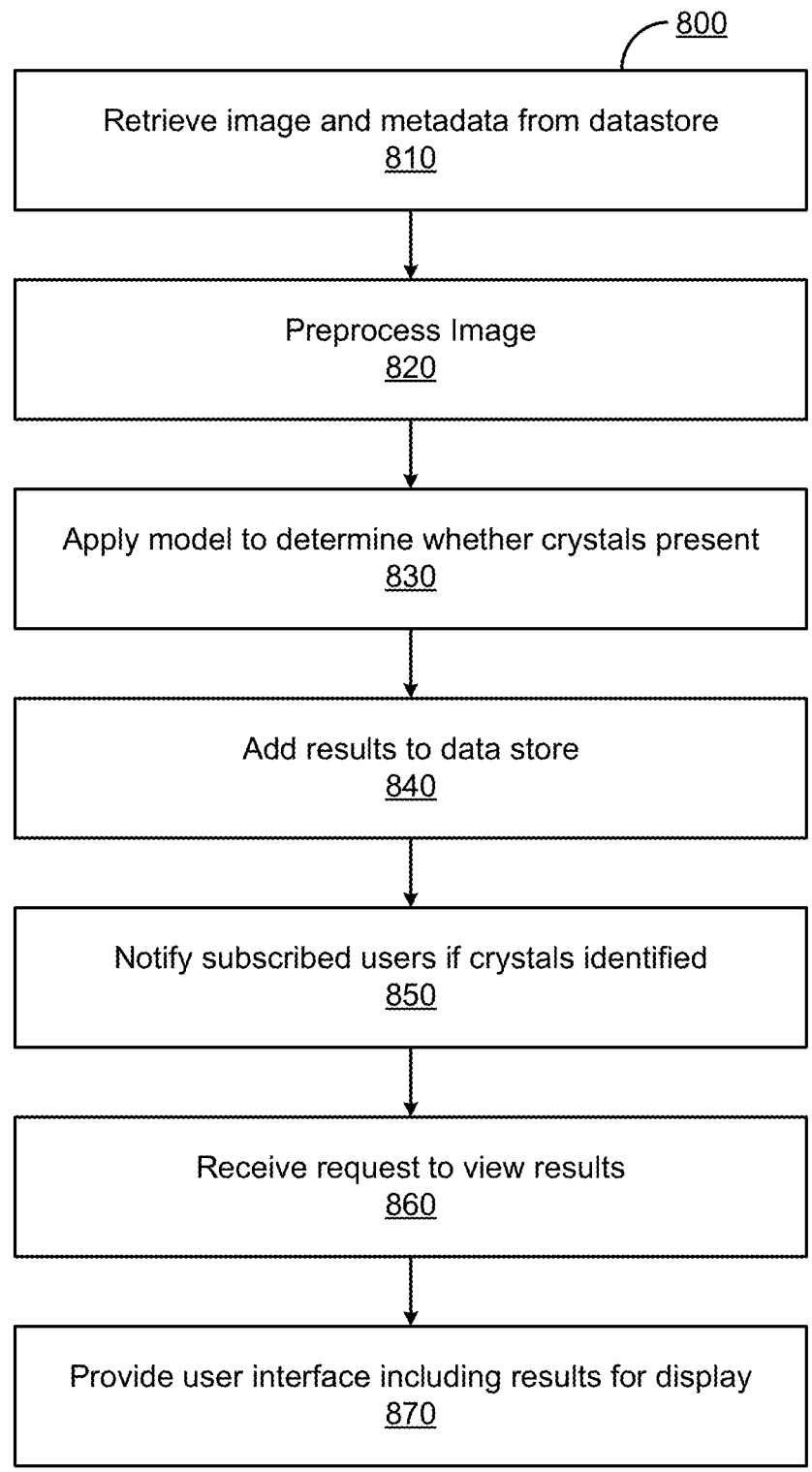
FIG. 8 is a flowchart illustrating an example method for automatically identifying protein crystallization trials in which crystals have formed, according to one embodiment.

FIG. 8 illustrates a method 800 for automatically identifying protein crystallization trials in which crystals have formed, according to one embodiment. The steps of FIG. 8 are illustrated from the perspective of various components of the image analysis system 140 performing the method 800. However, some or all of the steps may be performed by other entities and/or components. In addition, some embodiments may perform the steps in parallel, perform the steps in different orders, or perform different steps.

In the embodiment shown in FIG. 8, the method 800 begins with the image processing system 140 retrieving 810 an image depicting a protein crystallization trial drop from a data store (e.g., the laboratory datastore 130). Retrieval 810 of the image may be triggered by the scheduling module 410 (e.g., as part of a periodic image analysis cycle). The image processing system 140 may also retrieve some or all of the associated metadata.

The preprocessing module 420 preprocesses 820 the image in preparation for classification. As described previously, on one embodiment, the preprocessing 820 includes cropping, down-sampling, and converting the image to grayscale. In other embodiments, the preprocessing 820 may include different and/or additional processes.

The classification module 430 applies a machine-learned model to the image to determine whether crystals are present in the depicted drop. In one embodiment, the machine-learned model is a neural network (e.g., the neural network of FIG. 5) that has been trained to classify an input image in to one of a set of categories (e.g., the ten categories of FIG. 3). The set of categories may include one or more categories that correspond to protein crystallization and one or more categories that correspond to an absence of detectable protein crystallization. The model outputs a predicted category for the image. The predicted category may include a score indicating the likelihood that the prediction is correct. In some embodiments, the model outputs a score for each category indicating the likelihood that the image in question falls into the corresponding category.

The classification module 430 adds 840 results to a datastore (e.g., the laboratory database 130). In one embodiment, the results include the predicted category for the image and the associated score. Where the model outputs a score for each category, the results may include just the highest score, any score that exceeds a threshold, or all of the scores, depending on the specific embodiment.

The notification module 440 notifies 850 subscribed users if crystals are identified. For example, if the classification module 430 classifies the image as a crystal type 310. In one embodiment, the notification is sent as part of a periodic (e.g., daily) digest that identifies any images classified as a crystal type 310 for which the user is subscribed to receive updates. As described previously, the notification may include a link to access the results in more detail.

If the user interface module 450 receives 860 a request to view the results (e.g., as a result of a user clicking on a link included in a notification), the user interface module 450 provides 870 a user interface including the results for display (e.g., at a client device). In one embodiment, the provided user interface is the user interface described above with reference to FIG. 6. The user may then browse through the results (e.g., using controls on the user's client device 150) to obtain more information (e.g., What type of crystals were detected? How certain is the prediction? How long did crystallization take? What conditions led to crystallization? Etc.).

Example Machine Architecture

Figure 9:
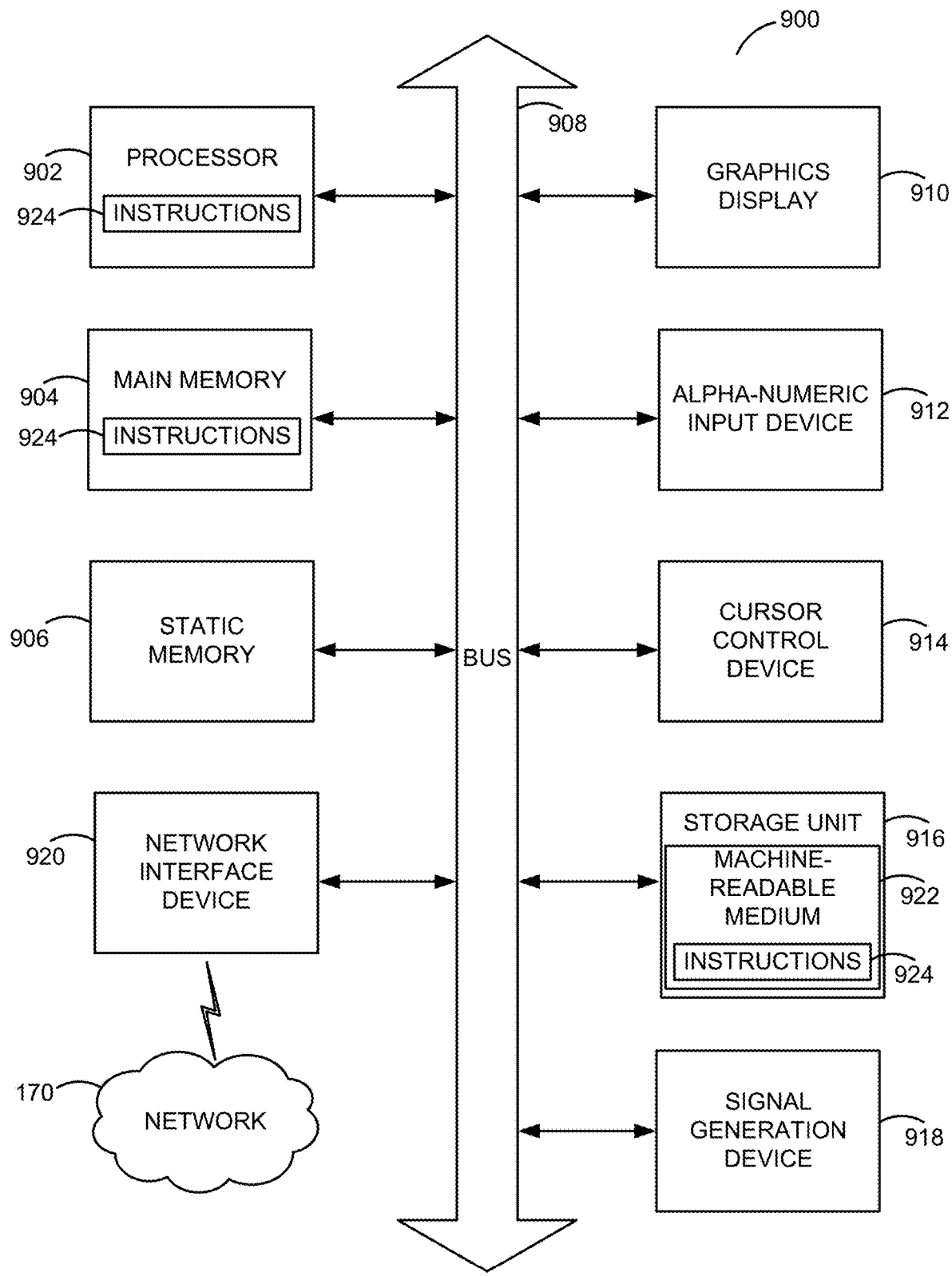
FIG. 9 is a block diagram illustrating components of an example machine able to read instructions from a machine-readable medium and execute them in a processor (or controller).

FIG. 9 is a block diagram illustrating components of an example machine able to read instructions from a machine-readable medium and execute them in a processor (or controller), according to one embodiment. Specifically, FIG. 9 shows a diagrammatic representation of a machine in the example form of a computer system 900. The computer system 900 can be used to execute instructions 924 (e.g., program label or software) for causing the machine to perform any one or more of the methodologies (or processes) described herein, such as methods 700 or 800. In some embodiments, the machine operates as a standalone device or a connected (e.g., networked) device that connects to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a smartphone, an internet of things (IoT) appliance, a network router, switch or bridge, or any machine capable of executing instructions 924 (sequential or otherwise) that specify actions to be taken by that machine. Further, while only a single machine is illustrated, the term "machine" shall also be taken to include any collection of machines that individually or jointly execute instructions 924 to perform any one or more of the methodologies discussed herein.

The example computer system 900 includes one or more processing units (generally processor 902). The processor 902 is, for example, one or more: central processing units (CPU), graphics processing units (GPUs), digital signal processors (DSPs), controllers, state machines, application specific integrated circuits (ASICs), radio-frequency integrated circuits (RFICs), or any combination of these. The computer system 900 also includes a main memory 904. The computer system may include a storage unit 916. The processor 902, memory 904, and the storage unit 916 communicate via a bus 908.

In addition, the computer system 900 can include a static memory 906 and a display driver 910 (e.g., to drive a plasma display panel (PDP), a liquid crystal display (LCD), or a projector). The computer system 900 may also include alphanumeric input device 912 (e.g., a keyboard), a cursor control device 914 (e.g., a mouse, a trackball, a joystick, a motion sensor, or other pointing instrument), a signal generation device 918 (e.g., a speaker), and a network interface device 920, which also are configured to communicate via the bus 908.

The storage unit 916 includes a machine-readable medium 922 on which is stored instructions 924 (e.g., the software modules described with reference to FIG. 4) embodying any one or more of the methodologies or functions described herein. The machine-readable medium 922 may be a non-transitory medium such as a hard drive, flash memory, a CD-ROM, a DVD, a floppy disk, or the like. The instructions 924 may also reside, completely or at least partially, within the main memory 904 or within the processor 902 (e.g., within a processor's cache memory) during execution thereof by the computer system 900, the main memory 904 and the processor 902 also constituting machine-readable media. The instructions 924 may be transmitted or received over a network 170 via the network interface device 920.

While machine-readable medium 922 is shown in an example embodiment to be a single medium, the term "machine-readable medium" should be taken to include a single medium or multiple media (e.g., a centralized or distributed database, or associated caches and servers) able to store the instructions 924. The term "machine-readable medium" shall also be taken to include any medium that is capable of storing instructions 924 for execution by the machine and that cause the machine to perform any one or more of the methodologies disclosed herein. The term "machine-readable medium" includes, but not be limited to, data repositories in the form of solid-state memories, optical media, and magnetic media.

ADDITIONAL CONSIDERATIONS

The disclosed approaches to automatic protein crystallization trial analysis provide various benefits and advantages. These include improving the functionality of protein trial systems by enabling automatic detection of drops that are likely to include crystals without human intervention. This may improve efficiency and free up crystallographer time for performing detailed analysis on protein crystals. This may also reduce the number of false positives and/or negatives as human operators, who are prone to errors (particularly after viewing and classifying many images), may focus their review on promising candidates.

Also disclosed are improved user interfaces that can provide more efficient interaction between protein trial systems and users. These user interfaces provide greater information and tools that enable more nuanced and intuitive analysis of results. For example, the user interface shown in FIG. 6 may enable a user to quickly filter down results to identify potential candidates and quickly identify the most promising candidates based on the provided information and any specific preferences of the user (e.g., preferring a particular pH range, being particularly time sensitive, etc.).

Throughout this specification, plural instances may implement components, operations, or structures described as a single instance. For example, any reference to a processor 902 may refer to a single processor or multiple processors. Although individual operations of one or more methods are illustrated and described as separate operations, one or more of the individual operations may be performed concurrently, and nothing requires that the operations be performed in the order illustrated. Furthermore, structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described as including logic or a number of components, modules, or mechanisms, for example, as illustrated in FIGS. 1, 4, and 5. Modules may constitute either software modules (e.g., code embodied on a machine-readable medium) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described may be performed, at least partially, by one or more processors, e.g., processor 902, that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among one or more processors, not only residing within a single machine, but deployed across a number of machines. In some example embodiments, one or more processors or processor-implemented modules may be located in a single geographic location (e.g., within a home environment, an office environment, or a server farm). In other example embodiments, one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition X or Y is satisfied by any one of the following: X is true (or present) and Y is false (or not present), X is false (or not present) and Y is true (or present), and both X and Y are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for proving that a target system 110 was configured as intended, according to an approved recipe 131, through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method of automatically analyzing protein crystallization trials, the method comprising:
   retrieving an image from a datastore, the image depicting a drop including a protein in solution;
   applying a neural network to the image, the neural network including a plurality of dimensionality reduction layer pairs and a plurality of fully connected layers, wherein an output of the neural network indicates a predicted classification of the image;
   determining, based on the predicted classification, whether the protein has crystallized in the drop;
   responsive to determining that the protein has crystallized in the drop:
      identifying a user subscribed to receive updates for a trial with which the image is associated;
      looking up contact information for the user; and
      sending a notification that the protein has crystallized in the drop to the user using the contact information; and
   providing a user interface for display at a client device responsive to the protein having crystallized, the user interface including information about the drop.

2. The method of claim 1, wherein each dimensionality reduction layer pair includes a convolution layer followed by a max-pooling layer.

3. The method of claim 1, wherein the plurality of dimensionality reduction layer pairs includes five dimensionality reduction layer pairs.

4. The method of claim 1, wherein the plurality of fully connected layers comprises four fully connected layers.

5. The method of claim 1, wherein the output of the neural network includes the predicted classification and a score indicating a likelihood that the predicted classification is correct.

6. The method of claim 1, wherein the output of the neural network includes a set of scores, each score indicating a likelihood that a corresponding one of a plurality of possible classifications is correct, the plurality of possible classifications including a plurality of crystal type classifications and a plurality of non-crystal type classifications.

7. The method of claim 1, wherein the neural network was trained by a process including:
labelling a training set of images, each image labelled with one of a plurality of classifications, the plurality of classifications including one or more crystal type classifications and one or more non-crystal type classifications;
augmenting the training set by generating synthetic images for the one or more crystal type classifications;
applying the neural network to the augmented training set to generate predicted classifications for the images, the predicted classifications selected from among the plurality of classifications; and
updating the model based on differences between the labels and the predicted classifications for the images in the training set.

8. The method of claim 7, wherein generating a synthetic image for a given classification comprises:
identifying an image labelled with the given classification;
rotating the identified image through a random angle;
flipping the identified image horizontally with a probability of 50%; and
flipping the identified image vertically with a probability of 50%.

9. The method of claim 1, wherein the user interface is provided for display at the client device responsive to user selection, at the client device, of a link included in the notification.

10. An automatic protein crystallization trial analysis system stored on a machine-readable storage medium, wherein the automatic protein crystallization trial analysis system is manufactured by a process comprising:
retrieving a training set of images from a datastore, each image depicting a drop including a protein in solution
labelling the images in the training set, each image labelled with one of a plurality of classifications, the plurality of classifications including one or more crystal type classifications and one or more non-crystal type classifications;
augmenting the training set by generating synthetic images for the one or more crystal type classifications, wherein generating a synthetic image comprises:
identifying an image labelled with the given crystal type classification;
rotating the identified image through a random angle;
flipping the identified image horizontally with a probability of 50%; and
flipping the identified image vertically with a probability of 50%; and
training a model, using the augmented training set, to classify images according to the plurality of classifications.

11. The automatic protein crystallization trial analysis system of claim 10, wherein training the model comprises:
applying the model to the augmented training set to generate predicted classifications for the images, the predicted classifications selected from among the plurality of classifications; and
updating the model based on differences between the labels and the predicted classifications for the images in the training set.

12. The automatic protein crystallization trial analysis system of claim 11, wherein training the model further comprises:
determining whether one or more training criteria are met for the model;
applying, responsive to the training criteria not being met, the updated model to the augmented training set to generate updated predicted classifications for the images; and
further updating the model based on differences between the labels and the updated predicted classifications.

13. The automatic protein crystallization trial analysis system of claim 10, wherein the model is a neural network including a plurality of dimensionality reduction layer pairs and a plurality of fully connected layers.

14. The automatic protein crystallization trial analysis system of claim 13, wherein the plurality of dimensionality reduction layer pairs includes five dimensionality reduction layer pairs, each pair including a convolution layer followed by a max-pooling layer, and the plurality of fully connected layers comprises four fully connected layers.

15. The automatic protein crystallization trial analysis system of claim 10, wherein the model is a ResNet-56 neural network.

16. A protein trial system comprising:
a camera configured to periodically capture images of protein drops of a protein trial;
a datastore, communicably coupled to the camera, configured to store the captured images;
an image analysis system, communicably coupled to the datastore, configured to:
apply a neural network to the captured images to generate predicted classifications for the captured images, the neural network including a plurality of dimensionality reduction layer pairs and a plurality of fully connected layers;
determine, based on the predicted classifications, whether protein crystallization has occurred in one or more of the protein drops; and
responsive to determining that protein crystallization has occurred in one or more of the protein drops:
identify a user subscribed to receive updates for the protein trial;
look up contact information for the user; and
send a notification that protein crystallization has occurred in one or more of the protein drops to the user using the contact information; and
a client device, communicably coupled to the image analysis system, configured to display a user interface, the user interface including the predicted classification of at least some of the captured images.

17. The protein trial system of claim 16, wherein the neural network was trained by a process including:
retrieving a training set of images from a datastore, each image depicting a drop including a protein in solution
labelling the images in the training set, each image labelled with one of a plurality of classifications, the plurality of classifications including one or more crystal type classifications and one or more non-crystal type classifications;

augmenting the training set by generating synthetic images for the one or more crystal type classifications; and training the neural network, using the augmented training set, to classify images according to the plurality of classifications, wherein the predicted classifications are selected from the plurality of classifications.

18. The protein trial system of claim 17, wherein the synthetic image for a given classification was generated by a process comprising:

identifying an image labelled with the given classification;

rotating the identified image through a random angle;

flipping the identified image horizontally with a probability of 50%; and flipping the identified image vertically with a probability of 50%.

19. The protein trial system of claim 16, wherein the model is a neural network including five dimensionality reduction layer pairs and a plurality of fully connected layers, each dimensionality reduction layer pair including a convolution layer followed by a max-pooling layer.

20. The protein trial system of claim 16, wherein the user interface is displayed at the client device responsive to user selection, at the client device, of a link included in the notification.

* * * * *

UNITED STATES PATENT AND TRADEMARK OFFICE
CERTIFICATE OF CORRECTION

PATENT NO. : 11,010,591 B2
APPLICATION NO. : 16/265730
DATED : May 18, 2021
INVENTOR(S) : Soheil Ghafurian et al.

Page 1 of 1

It is certified that error appears in the above-identified patent and that said Letters Patent is hereby corrected as shown below:

On the Title Page

Item (56), in Column 2, under "Other Publications", Line 1, delete "Tensofflow:" and insert -- Tensorflow: --, therefor.

In the Claims

In Column 17, in Claim 10, Line 47, after "solution" insert -- ; --.

In Column 18, in Claim 17, Line 62, after "solution" insert -- ; --.

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*